United States Patent [19]
McClure et al.

[11] Patent Number: 6,047,215
[45] Date of Patent: Apr. 4, 2000

[54] METHOD AND APPARATUS FOR ELECTROMAGNETICALLY ASSISTED LIPOSUCTION

[75] Inventors: Richard J. McClure, San Diego; R. Kemp Massengill, Poway, both of Calif.

[73] Assignee: Sonique Surgical Systems, Inc., Escondido, Calif.

[21] Appl. No.: 09/036,295

[22] Filed: Mar. 6, 1998

[51] Int. Cl.[7] .................................................. A61B 17/39
[52] U.S. Cl. ............................ 607/101; 607/155; 607/99
[58] Field of Search ................................... 607/101–102, 607/104, 154–156

[56] References Cited

U.S. PATENT DOCUMENTS

| | | | |
|---|---|---|---|
| 4,397,313 | 8/1983 | Vaguine .................................. | 607/101 |
| 4,583,556 | 4/1986 | Hines et al. . | |
| 4,819,642 | 4/1989 | Andersen et al. ....................... | 607/101 |
| 4,825,880 | 5/1989 | Stauffer et al. . | |
| 4,886,491 | 12/1989 | Parisi et al. . | |
| 4,974,587 | 12/1990 | Turner et al. ........................... | 607/101 |
| 5,143,063 | 9/1992 | Fellner . | |
| 5,295,955 | 3/1994 | Rosen et al. . | |
| 5,501,655 | 3/1996 | Rolt et al. . | |
| 5,503,150 | 4/1996 | Evans . | |
| 5,507,790 | 4/1996 | Weiss . | |
| 5,549,639 | 8/1996 | Ross . | |
| 5,573,497 | 11/1996 | Chapelon . | |
| 5,660,836 | 8/1997 | Knowlton . | |
| 5,683,382 | 11/1997 | Lenihan et al. . | |
| 5,683,384 | 11/1997 | Gough et al. . | |
| 5,688,267 | 11/1997 | Panescu et al. . | |
| 5,690,614 | 11/1997 | Carr et al. . | |

(List continued on next page.)

FOREIGN PATENT DOCUMENTS

| | | |
|---|---|---|
| 0 617 599 | 10/1996 | European Pat. Off. . |
| WO 97/25919 | 7/1997 | WIPO . |
| WO 97/40882 | 11/1997 | WIPO . |
| WO 97/41800 | 11/1997 | WIPO . |

OTHER PUBLICATIONS

Bommannan; Sonophoresis I, The Use of High–Frequency Ultrasound to Enhance Transdermal Drug Delivery; Pharmaceutical Research, vol. 9, No. 4; pp. 559–564; 1992.

Dickinson; Measurement of Changes in Tissue Temperature Using MR Imaging; Journal of Computer Assisted Tomography, 10(3); pp. 468–472; 1986.

Finger; Microwave Thermoradiotherpy for Uveal Melonoma, Results of a 10 Year Study; Ophthalmology, vol. 104, No. 11; pp. 1794–1803; Nov., 1997.

Harvey; Industrial, Biological, and Medical Aspects of Microwave Radiation; Royal Radar Establishment; pp. 557–566; 1959.

Hunt; Priniciples of Ultrasound Used for Generating Localized Hyperthermia; Introduction to Practical Aspects of Clinical Hyperthermia, Taylor and Francis; pp. 371–422; 1990.

(List continued on next page.)

*Primary Examiner*—Linda C. M. Dvorak
*Assistant Examiner*—Roy Gibson
*Attorney, Agent, or Firm*—Gerald W. Spinks

[57] ABSTRACT

An improved method and apparatus for facilitating removal of fat from obese, or lipodystrophic patients, by external application of electromagnetic energy. After infiltrating the proposed zone with intumescing solution, radio frequency or microwave electromagnetic energy is applied via externally placed applicators to the body site of unwanted fatty tissue. The electromagnetic energy supplies heat to the fatty tissue and to the intumescing solution, aiding in subsequent fat removal by conventional, or preferably, ultrasound-assisted, or microwave-assisted, internal liposuction. Depth of tissue penetration is controllable by selection of the appropriate electromagnetic frequency and by varying the configuration of the applicators. Restricting the intumescing procedure to only the desired body sites subject to subsequent internal surgical intervention reduces unwanted heating of the underlying muscle or other organs. Multiple-frequency capability is incorporated in the power supply.

8 Claims, 2 Drawing Sheets

U.S. PATENT DOCUMENTS

| | | |
|---|---|---|
| 5,693,078 | 12/1997 | Desai et al. . |
| 5,693,082 | 12/1997 | Warner et al. . |
| 5,769,879 | 6/1998 | Richards et al. .......................... 607/101 |

OTHER PUBLICATIONS

Luxar Silhouette Product Summary; 11 pages; 1996.

Osepchuk; Microwave Technology; Kirk–Othmer Encyclopedia of Chemical Technology, Fourth Edition, vol. 16, John Wiley & Sons, Inc.; pp. 672–700; 1995.

Schwan; Variations Between Measured and Biologically Effective Microwave Diathermy Dosage; Archives of Physical Medicine & Rehabilitation; pp. 363–370; Jun., 1955.

Silberg; Look as Good as You Feel; http://www.silberg.com; Dec., 1997 (six page printout provided).

Wang; Computationally Efficient Algorithms for Control of Ultrasound Phased–Array Hyperthermia Applicators Based on a Pseudoinverse Method; IEEE Transactions on Ultrasonics, Ferroelectrics, and Frequency Control, vol. 37, No. 2; pp. 274–277; 1990.

METHOD AND APPARATUS FOR ELECTROMAGNETICALLY ASSISTED LIPOSUCTION

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention is in the field of removal of excess fat by liposuction.

2. Background Information

Liposuction, the surgical procedure for removal of excess fat from storage sites in the body, has grown in popularity with the surge of obesity in the population. Invention of the ultrasonically assisted liposuction apparatus, for example U.S. Pat. No. 4,886,491 to Parisi and Massengill, has made it possible to remove many kilograms of fat in a single procedure, with comparative safety. As removal of fat cells (adipocytes) is permanent, ultrasonic liposuction procedures may well be preferred to repetitive, and generally ineffective, dieting.

Intumescing, or addition of aqueous solutions of various agents to the tissue, is often done prior to the liposuction procedure. Using an ultrasonically assisted internal liposuction modality, the addition of fluid allows for emulsification and easier removal of the fat and liquid aggregate, which has a lower viscosity than fat alone. By localizing the placement and the quantity of the intumescing fluid, treatment specificity and greater surgical precision are realized. The ultrasonic energy provided by the liposuction cannula breaks down the adipocyte cell wall through a combination of mechanisms, including significant localized frictional heat to "melt" the tissue, as well as mechanical tissue separation. The consequence of these effects is that viscous fat within the adipocyte is liberated, and aspiration is facilitated, as compared to a liposuction procedure in which intumescence is not employed.

Silberg has designed and commercialized an externally applied ultrasonic device, to be used after intumescing and prior to conventional liposuction, to aid in preparation for fat removal. The actual liposuction is performed with a conventional suction-only liposuction cannula. Silberg's apparatus provides ultrasonic energy to the patient via an applicator having a surface contact area of 5 or 10 square centimeters. The power is limited to a level less than that which will cause distress to the skin, which appears to be about 100 to 200 watts, or 20 watts per square centimeter, maximum.

Because of physical limitations, such as the inability to achieve high power densities, as well as the need to maintain intimate physical contact with the skin to allow energy coupling to the underlying tissues, it is necessary to apply the ultrasound energy with Silberg's device for a considerable period of time, sometimes for over three minutes at each proposed removal site.

U. S. Pat. No. 5,507,790 to Weiss discloses the use of externally applied electromagnetic or ultrasonic energy to accelerate local fat tissue lipolysis reaction rates. The Weiss patent, however, does not incorporate intumescence, or liposuction, whether with or without the internal application of ultrasonic energy.

BRIEF SUMMARY OF THE INVENTION

The presently-disclosed method and device utilizes externally applied radio-frequency (R-F) electromagnetic energy, such as microwave energy, to treat the fatty tissue between the skin and the underlying muscle plane, rendering the fatty tissue more susceptible to removal with an internal, ultrasonically assisted or microwave assisted, liposuction cannula. An appropriate source of R-F energy, such as a waveguide or antenna array, is applied at, or near to, the external surface of the body in the region where the fatty tissue is to be treated. Intumescence of the treatment area is incorporated to facilitate the effect of the externally applied R-F energy.

Several significant advantages are apparent with the present invention. A first advantage is that depth of the R-F treatment may be controlled by selection of a specific, predetermined radio frequency. The overriding concern of the FDA and other regulatory agencies, both in the United States and internationally, is for safety. With this in mind, currently allowed frequencies in the United States for microwave appliances include 915 megahertz and 2450 megahertz. Initial embodiments of the present invention utilize these frequencies, since they are allowed for general consumer use and considered safe by the FDA. A frequency of 915 megahertz is preferred for deeper penetrations, and a frequency of 2450 megahertz is preferred for shallower penetrations. By way of example, a patient suffering from gross obesity, and thereby having a thick layer of fatty tissues, would be advantageously treated with equipment in the lower radio-frequency range, while a thin patient with small but abnormal fatty depositions, such as in lipodystrophy, would benefit from treatment with equipment in the higher radio-frequency range. As a practical consideration, it should be noted that 2450 megahertz equipment is more readily available, and less expensive, than equipment employing 915 megahertz, or other allowed frequencies. The use of other radio frequencies is within the scope of this disclosure, however, and may be employed in the practice of this invention.

To take advantage of the different penetration effects noted between 915 megahertz and 2450 megahertz, dual-frequency capability can be incorporated in the power supply of the proposed invention. This provision for selecting the frequency of the R-F radiation allows the surgeon to achieve the desired depth of penetration to treat the fatty tissue rapidly and efficiently, while avoiding overheating the underlying tissue, such as muscle or vital organs. Other multiple-frequency equipment also may be developed within the spirit of the present invention, as other frequencies gain regulatory acceptance.

A second advantage of the present invention is that power level and power density are also controllable for specific applications. This is an important feature, because treatment of thin layers of fat at a lower power level may be required for contouring or sculpting, while treatment of thick layers of fat at a higher power level may be required for obesity reduction. On the other hand, the power density which is acceptable for human surgery is limited to the level at which heat generated at the skin surface can be removed without an excessive temperature rise, as excessive temperature rise in the skin results in pain. Provision is made in the present invention for selecting the power level of the R-F radiation and controlling the configuration of the applicator elements, to achieve the desired depth of penetration to treat the fatty tissue rapidly and efficiently, while avoiding overheating the overlying skin or underlying tissue, such as muscle or vital organs.

Average power level may be varied by controlling the frequency of an on/off duty cycle. Power density may be maintained at an acceptable level by appropriate design of the size, shape, and arrangement of antenna or waveguide elements. Various other means can also be used to reduce unwanted temperature rise in the skin, including application of direct air cooling, regulation of the average power level, spacing of the applicators from the skin, and application of a non-aqueous emollient. Further, the applicator elements can be designed to reduce non-uniform power flux, which helps to avoid local heating of the skin. Finally, appropriate physical spacing between the applicator elements and the surface of the skin is designed into the preferred embodiment, to limit skin temperature.

A third, and perhaps the most important, advantage of the present invention is achieved by utilization of the fact that R-F energy couples more readily with water molecules than with biological tissues. This phenomenon is not seen with externally applied ultrasonic energy. In the present invention, aqueous solutions are introduced into the treatment area to take advantage of this phenomenon. Water molecules are present within the intumescing fluid and within the adipocytes themselves. This results in heating of both the intumescing fluid and the adipocytes. Such heating weakens the adipocyte cell walls and decreases the viscosity of the fatty material within the adipocytes. Because of these effects, subsequent internal liposuction is facilitated, and surgical time is conserved. Especially where the internal liposuction is ultrasonically-assisted or microwave-assisted, the surgeon experiences less fatigue, as the internal liposuction cannula encounters less friction in the back-and-forth, in-and-out surgical movements.

Restriction of the intumescing procedure to only the areas targeted for subsequent internal liposuction ("intumescing localization") allows the use of higher power levels, because the intumescence limits R-F penetration, thereby helping to protect the tissues underlying the fatty layer. Unlike externally-applied ultrasonic energy, which couples poorly with intumescing solution, localization of intumescence creates an excellent advantage for externally-applied R-F energy, in that coupling can be differentially increased, or limited, merely by placing more or less intumescent fluid in a given body location. As an example, skin burning tends to be limited with the present invention, since skin tissue contains relatively little water, and it therefore experiences less heating by the R-F energy. This safety feature is enhanced by the fact that the skin is not directly intumesced during the surgical procedure, as is the fatty tissue.

Through the proper application of localized intumescence and the proper design of applicator elements, the apparatus of the present invention can supply 1 kilowatt of power, if needed, to an applicator of 5 square centimeters, for a power density of 200 watts per square centimeter. Because the power is adjustable and can be much higher than the permissible externally applied ultrasonic power, the surgical procedure time may be significantly reduced by the apparatus of the present invention.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
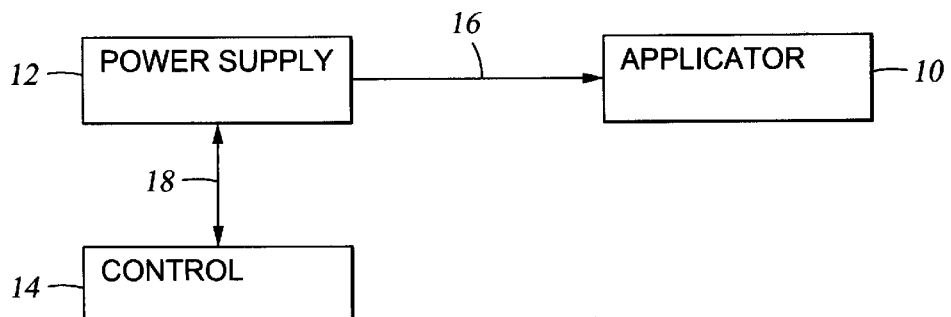
FIG. 1 is a schematic view of the apparatus of the present invention.

As shown in FIG. 1, the apparatus of the present invention includes a microwave applicator 10, a power supply 12, and a controller 14. The power supply 12 generates radio-frequency energy which is transmitted to the applicator 10 by a coaxial cable 16. The instantaneous power level and duty cycle frequency of the energy generated by the power supply 12 are controlled by the surgeon via the controller 14. The duty cycle frequency is set to be appropriate for the size and location of the fatty tissue mass, while the instantaneous power level is selected to suit the depth and shape of the fatty tissue. Dual-frequency, or multiple-frequency, R-F capabilities can be incorporated, by means well known in the art. For example, frequencies of 915 MHz and 2450 MHz would be suitable. A representative power level for the power supply 12 would be 1 kilowatt.

Figure 2:
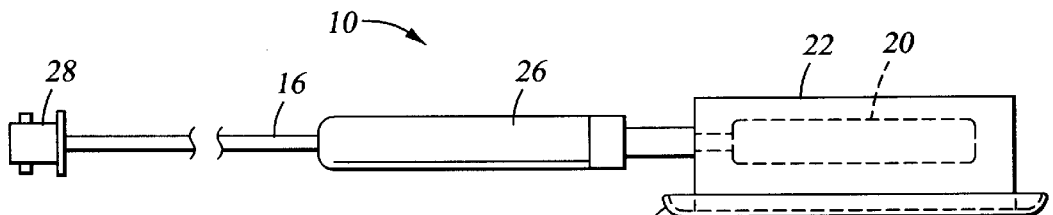
FIG. 2 is a side view of an external R-F applicator embodiment according to the present invention.

As shown in FIG. 2, the applicator 10 includes at least one antenna 20 for emitting electromagnetic energy, a radiation shield 22 made of material substantially impermeable to the electromagnetic energy, and a contact plate 24 made of material substantially permeable to the energy. The shield 22 is shaped to substantially surround the antenna 20 on all but one side, to protect a user of the apparatus from unnecessary exposure to the electromagnetic radiation, while directing the electromagnetic radiation toward the treatment area of a patient's body. The contact plate 24 can have upturned edges, forming a rounded skirt, to make the contact plate more suitable for contact with the skin of the patient. A handpiece 26 can also be coupled mechanically to the antenna 20 via a flexible, hinge-like member which allows the antenna 20 to pivot and follow body contours of a patient. A connector 28 can be provided at one end of the coaxial cable 16 for connecting the coaxial cable 16 to the power supply 12.

Figure 3:
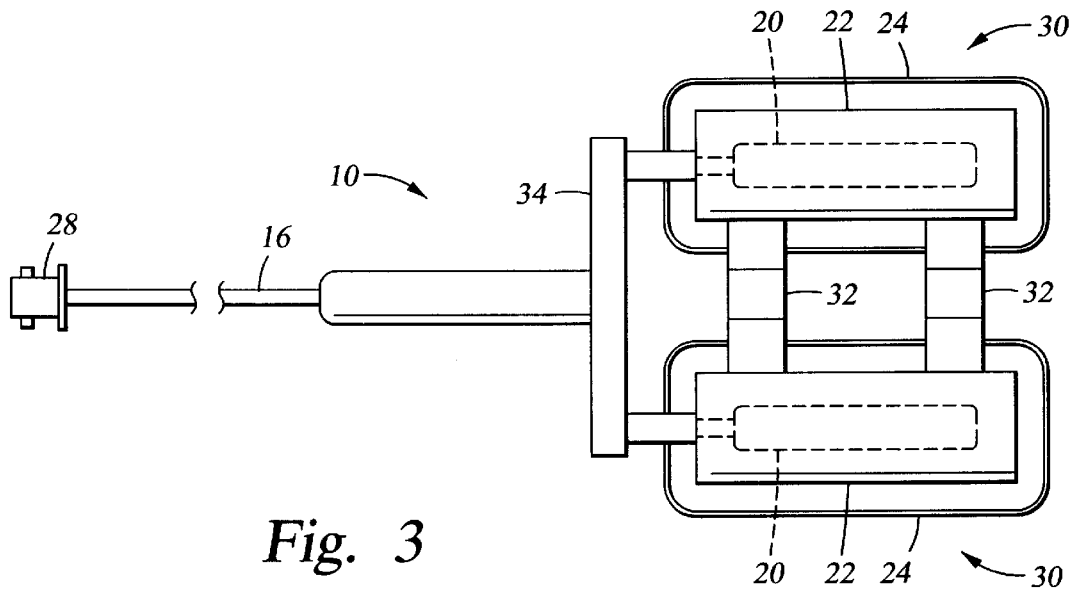
FIG. 3 is a plan view of the dual element external R-F applicator embodiment according to the present invention.

FIG. 3 shows that the applicator 10 can ideally have two antennae 20. A separate shield 22 substantially surrounds each antenna 20, and a separate contact plate 24 is provided for each antenna 20. In this embodiment, each antenna 20 and its related shield 22 and contact plate 24 constitute an applicator paddle 30. The two paddles 30 of the applicator 10 are joined by one or more flexible connecting members 32 and a flexible coax splitter 34 in such a way that the paddles 30 can pivot about a longitudinal axis parallel to the longitudinal axes of the antennae 20. Pivoting about other axes may also be provided. This allows for conformity with the patient's body shape in at least one axis, and it allows for the energy radiated by the two paddles 30 to be overlapped at a desired treatment site in the fatty tissue, as will be discussed below.

Figure 4:
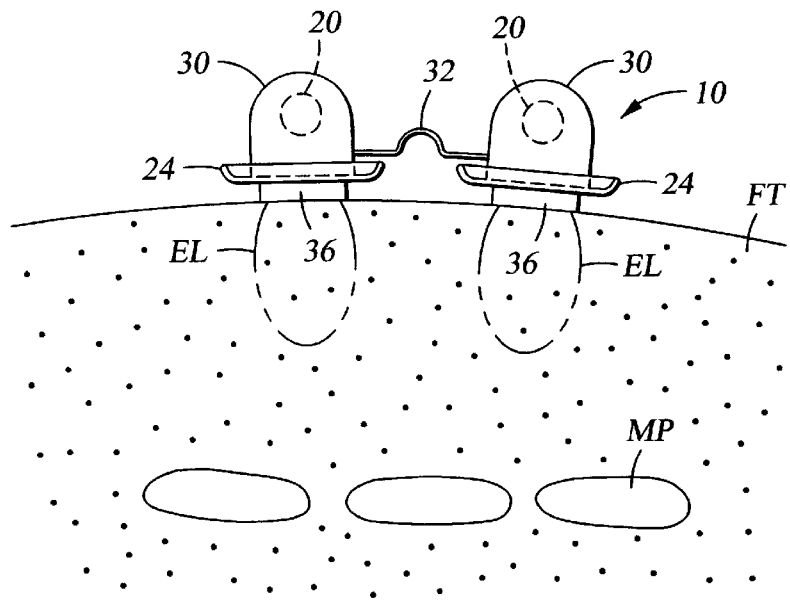
FIG. 4 is a schematic view of energy distribution lobes as applied by the dual element external R-F applicator shown in FIG. 3.

As shown in FIG. 4, the two paddles 30 of the applicator 10 can be spaced from the skin of the patient by spacers 36. These spacers 36 can assist in protecting the skin of the patient from an excessive temperature rise, by simply spacing the paddles 30 from the skin. Each antenna 20 generates an energy lobe EL of electromagnetic energy, preferably in the microwave range. The depth and width of each energy lobe EL into the fatty tissue FT depends upon several factors, including the frequency, the instantaneous power level, the duty cycle, the distance of the antenna 20 from the skin, and the degree of intumescence of the fatty tissue FT. Typically, these factors will be controlled as discussed above, to insure that the energy lobes EL impose sufficient electromagnetic energy on the fatty tissue FT to cause the adipocytes to begin to break down, without having an appreciable effect on the skin or on the tissue in the muscle plane MP.

Figure 5:
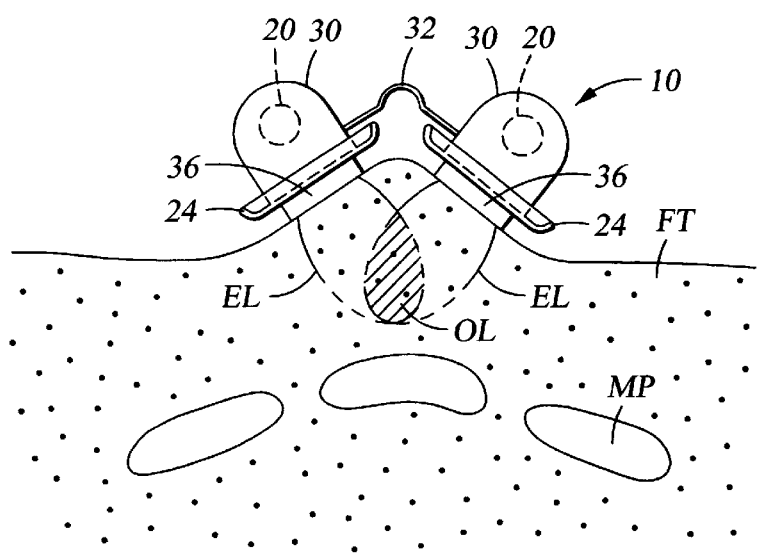
FIG. 5 is a schematic view of overlapping energy distribution lobes as applied by angling the dual R-F applicator elements toward each other.

As shown in FIG. 5, by rotation of the paddles 30 inwardly, the physician can direct the energy lobes EL generated by the paddles 30 toward each other, causing the energy lobes EL to be overlapped so that the power delivered to the overlap region OL is increased. This technique can be used to deliver a desired power level to the target tissue in the overlap region OL without imposing an excessive power level on intervening tissues, such as the skin. The paddles 30 can be manipulated to capture a desired portion of the fatty tissue FT between the paddles 30 as shown, to create the overlap region OL where desired.

Figure 6:
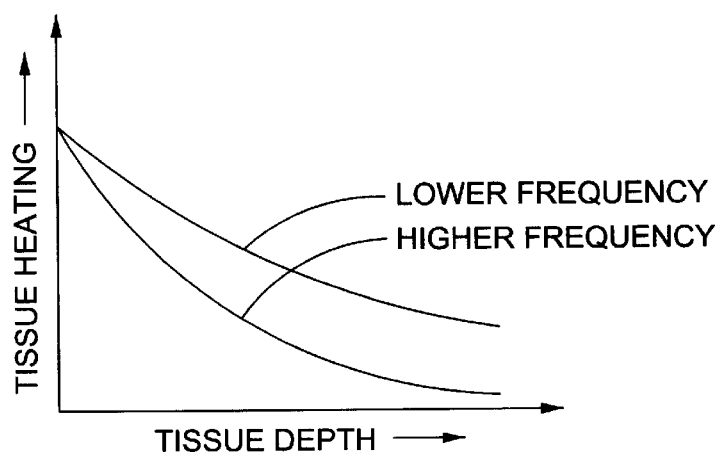
FIG. 6 is a graph of tissue heating versus tissue depth.

As shown in FIG. 6, depth of penetration of the heating power of each energy lobe EL into the fatty tissue FT varies with R-F frequency. Hence, control for depth may be provided by selecting the most appropriate frequency for the degree of obesity to be treated. The other parameters, including instantaneous power level, duty cycle, spacing from the skin, and degree of intumescence are used in conjunction with selection of the appropriate frequency to achieve the desired over all effect, which varies with the nature of each region of fatty tissue FT being treated.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for preconditioning fatty tissue for liposuction, said apparatus comprising:
    a source of R-F energy;
    an applicator body;
    a first antenna mounted to said applicator body, said first antenna being transmissively connected to said R-F source;
    a first R-F shield mounted to said first antenna, said first R-F shield being constructed of a material impermeable to R-F radiation, said first R-F shield being shaped, sized, and positioned to shield a user of said apparatus from R-F radiation and to direct R-F radiation from said first antenna in a first selected direction;
    a second antenna mounted to said applicator body independently of said first antenna, said second antenna being transmissively connected to said R-F source;
    a second R-F shield mounted to said second antenna independently of said first R-F shield, said second R-F shield being shaped, sized, and positioned to shield a user of said apparatus from R-F radiation and to direct R-F radiation from said second antenna in a second selected direction; and
    a flexible connecting member on said applicator body, said flexible member connecting said first and second antennae together, said flexible connecting member being adapted to allow independent orientation of said first and second antennae in different said first and second directions.

2. An apparatus as recited in claim 1, further comprising:
    a first spacer on said first antenna for spacing said first antenna a sufficient distance from the skin of a patient to prevent burning of the skin at the maximum power level of said R-F source; and
    a second spacer on said second antenna for spacing said second antenna a sufficient distance from the skin of a patient to prevent burning of the skin at the maximum power level of said R-F source.

3. An apparatus as recited in claim 1, further comprising:
    a first contact plate on said first antenna for contacting the skin of a patient, said first contact plate being constructed of a material substantially permeable to R-F radiation; and
    a second contact plate on said second antenna for contacting the skin of a patient, said second contact plate being constructed of a material substantially permeable to R-F radiation.

4. An apparatus as recited in claim 1, further comprising a controller for varying the radio frequency of said R-F source, to thereby control the depth of heating in the fatty tissue of a patient.

5. An apparatus as recited in claim 1, further comprising a controller for varying the power level of said R-F source, to thereby control the instantaneous power level and the power density emitted by said at least one antenna.

6. An apparatus as recited in claim 1, further comprising a controller for energizing and de-energizing said at least one antenna at selected intervals, to thereby control the average power level of R-F radiation emitted by said at least one antenna.

7. An apparatus for preconditioning fatty tissue for liposuction, said apparatus comprising:
    a source of R-F energy;
    a controller for varying the radio frequency and power level of said R-F source;
    an applicator body;
    first and second antennae independently mounted to said applicator body, each said antenna being transmissively connected to said R-F source, said first and second antennae being connected by a flexible connecting member adapted to allow independent orientation of said first and second antennae in different selected first and second directions;
    first and second R-F shields mounted to said first and second antennae respectively, said first and second R-F shields being constructed of a material impermeable to R-F radiation, said first and second R-F shields being shaped, sized, and positioned to shield a user of said apparatus from R-F radiation and to direct R-F radiation from said first and second antennae in said different selected first and second directions; and
    first and second contact plates on said said first and second antennae respectively for contacting the skin of a patient, said contact plates being constructed of a material substantially permeable to R-F radiation.

8. An apparatus for preconditioning fatty tissue for liposuction, said apparatus comprising:

a source of aqueous fluid for injection into selected fatty tissue of a patient;

at least one of R-F energy;

an applicator body;

at least one antenna mounted to said applicator body, said at least one antenna being transmissively connected to said R-F source; and at least one R-F shield mounted to said applicator, said at least one R-F shield being constructed of a material impermeable to R-F radiation, said at least one R-F shield being shaped, sized, and positioned to shield a user of said apparatus from R-F radiation and to direct R-F radiation from said at least one antenna into selected intumescent fatty tissue of a patient.

* * * * *